US007623615B2

(12) United States Patent
Kawachi et al.

(10) Patent No.: US 7,623,615 B2
(45) Date of Patent: Nov. 24, 2009

(54) X-RAY CT IMAGE RECONSTRUCTION METHOD AND X-RAY CT SYSTEM

(75) Inventors: Naoyuki Kawachi, Tokyo (JP); Tetsuya Horiuchi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/436,815

(22) Filed: May 18, 2006

(65) Prior Publication Data

US 2006/0262895 A1    Nov. 23, 2006

(30) Foreign Application Priority Data

May 20, 2005    (JP)    ............................ 2005-148346

(51) Int. Cl.
A61B 6/00    (2006.01)
(52) U.S. Cl. ............................................. 378/4; 378/15
(58) Field of Classification Search ............... 378/4–20, 378/901
See application file for complete search history.

(56) References Cited

U.S. PATENT DOCUMENTS

| 4,841,553 | A | * | 6/1989 | Nagai ........................... 378/19 |
| 5,065,436 | A | | 11/1991 | Matsumura .................. 382/131 |
| 5,524,130 | A | * | 6/1996 | Ohhashi ....................... 378/15 |
| 5,796,803 | A | * | 8/1998 | Flohr et al. ................... 378/15 |
| 5,881,122 | A | * | 3/1999 | Crawford et al. ............... 378/4 |
| 5,887,047 | A | * | 3/1999 | Bailey et al. .................... 378/4 |
| 5,946,371 | A | * | 8/1999 | Lai ............................... 378/19 |
| 5,953,388 | A | | 9/1999 | Walnut et al. .................. 378/4 |
| 5,960,056 | A | * | 9/1999 | Lai ................................ 378/4 |
| 6,002,738 | A | | 12/1999 | Cabral et al. ................... 378/4 |
| 6,201,849 | B1 | * | 3/2001 | Lai ................................ 378/4 |
| 6,269,141 | B1 | * | 7/2001 | Proksa et al. ................. 378/19 |
| 6,275,561 | B1 | * | 8/2001 | Danielsson .................. 378/15 |
| 6,285,733 | B1 | * | 9/2001 | Proksa et al. ................. 378/15 |
| 6,411,670 | B1 | * | 6/2002 | Besson ........................... 378/4 |
| 6,415,012 | B1 | | 7/2002 | Taguchi et al. ................ 378/15 |
| 6,625,249 | B1 | | 9/2003 | Temkin et al. .................. 378/4 |
| 6,775,347 | B2 | * | 8/2004 | Hsieh et al. ................... 378/15 |
| 6,829,325 | B2 | | 12/2004 | Shida et al. ..................... 378/4 |
| 2003/0118146 | A1 | | 6/2003 | Shida et al. ..................... 378/4 |

(Continued)

OTHER PUBLICATIONS

Radiological Modality Engineering (Medical, Dental & Pharmacological Publishing, Apr. 20, 2003, pp. 174-174.

(Continued)

*Primary Examiner*—Edward J Glick
*Assistant Examiner*—Alexander H Taningco
(74) *Attorney, Agent, or Firm*—Armstrong Teasdale LLP

(57) ABSTRACT

An X-ray CT image reconstruction method includes turning a fan-shaped X-ray beam, which is thick and irradiated to a subject, about the subject, detecting projection data items concerning an X-ray beam, which is transmitted by the subject, with the X-ray beam turned by a plurality of successive angles of rotation, enhancing fan-beam data, which includes projection data items detected with the X-ray beam turned by the angles of rotation, so as to sharpen projection data contained in the fan-beam data and acquired along each projection line, producing parallel-beam data, which has values thereof defined along parallel projection lines, in relation to each angle of projection using the enhanced fan-beam data, and reconstructing an image using the parallel-beam data.

16 Claims, 13 Drawing Sheets

U.S. PATENT DOCUMENTS

2003/0223533 A1* 12/2003 Hsieh et al. .................. 378/19
2004/0066879 A1   4/2004 Machida ....................... 378/4
2004/0199066 A1  10/2004 Kawachi et al. ............ 600/407
2005/0100124 A1*  5/2005 Hsieh et al. .................... 378/4

OTHER PUBLICATIONS

Image Processing Modality (by Tsuneo Saitoh, Modern Science Publishing, Mar. 10, 1993, pp. 107-108.

* cited by examiner

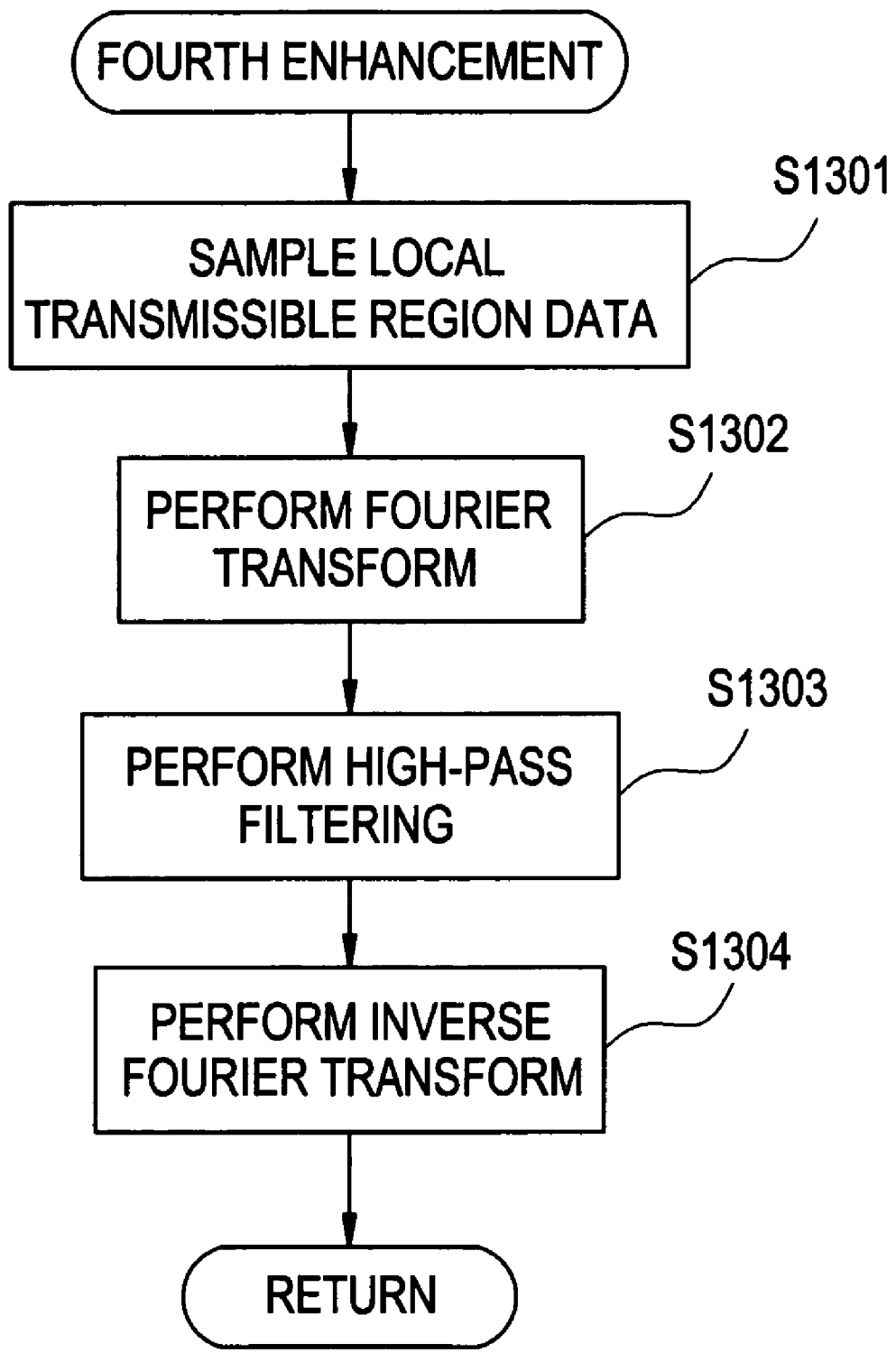

X-RAY CT IMAGE RECONSTRUCTION METHOD AND X-RAY CT SYSTEM

CROSS REFERENCE TO RELATED APPLICATIONS

This application claims the benefit of Japanese Application No. 2005-148346 filed May 20, 2005.

BACKGROUND OF THE INVENTION

The present invention relates to an X-ray CT image reconstruction method and an X-ray CT system in which fan-beam data concerning an X-ray beam that fans out is converted into parallel-beam data concerning parallel X-rays, which are supposed to be projected at an equal angle of projection, in order to reconstruct an image.

Recently, X-ray CT systems use three-dimensional tomographic image data of a subject to produce information on a projection image formed by projecting the three-dimensional tomographic image data in one direction. Methods for producing the information on a projection image include a maximum intensity projection (MIP) method of visualizing maximum pixel values detected in a direction of projection (refer to, for example, Non-patent Document 1).

When the MIP method is adopted, striped artifacts appear on a projection image. In efforts to minimize the striped artifacts, fan-beam data concerning an X-ray beam that fans out is converted into parallel-beam data concerning an X-ray beam, which is supposed to include parallel X-rays, in units of a projection line. The parallel-beam data is used to reconstruct an image (refer to, for example, Patent Document 1).

[Patent Document 1] Japanese Unexamined Patent Publication No. Sho 59(1984)-0168840 (pp. 3 and 4, FIGS. 2 and 3)

[Non-patent Document 1] "Radiological Modality Engineering" (Medical, Dental & Pharmacological Publishing, Apr. 20, 2003, pp. 174-175)

[Non-patent Document 2] "Image Processing Algorithm" (by Tsuneo Saitoh, Modern Science Publishing, Mar. 10, 1993, pp. 107-108)

However, according to the foregoing background art, the spatial resolution of a tomographic image gets poorer at a point in the image farther away from a point therein associated with a scan center position. In other words, the tomographic image becomes streamy towards the perimeter of a circle, of which center point is associated with the scan center position, proportionally to a distance from the point associated with the scan center position.

In particular, a tomographic image expressing the lung field radiographed through high-resolution CT examination contains an outstandingly streamy image in which blood capillaries existing in the lung field that are shown to be streamy towards the perimeter of a circle whose center is associated with a scan center position. Thus, the image quality is markedly poor.

Consequently, what counts with an X-ray CT image reconstruction method and an X-ray CT system is whether or not to be able to reduce a decrease in a resolution, which gets poorer proportionally to an increase in a distance of a point in a tomographic image from a point therein associated with a scan center position, occurring in case projection lines are converted from one form to another.

SUMMARY OF THE INVENTION

Therefore, an object of the present invention is to provide an X-ray CT image reconstruction method and an X-ray CT system capable of reducing a decrease in a resolution, which gets poorer proportionally to an increase in a distance of a point in a tomographic image from a point therein associated with a scan center position, occurring in case projection lines are converted from one form to another.

In efforts to solve the foregoing problem and accomplish the object, according to the first aspect of the invention, there is provided an X-ray CT image reconstruction method in which: a fan-shaped X-ray beam that is thick and irradiated to a subject is turned about the subject's periphery; projection data items concerning an X-ray beam transmitted by the subject are detected with the X-ray beam turned by a plurality of successive angles of rotation; fan-beam data including projection data items detected with an X-ray beam turned by the angles of rotation is enhanced in order to sharpen projection data contained in the fan-beam data and acquired along each projection line; the enhanced fan-beam data is used to produce parallel-beam data, which has values thereof defined along parallel projection lines, in relation to each angle of projection; and the parallel-beam data is used to reconstruct an image.

According to the first aspect of the present invention, after fan-beam data is enhanced, parallel-beam data is produced in order to reconstruct an image.

According to the second aspect of the present invention, there is provided an X-ray CT image reconstruction method identical to the X-ray CT image reconstruction method according to the first aspect of the present invention except that the enhancement includes the first enhancement of sharpening projection data items contained in a plurality of fan-beam data items detected with an X-ray beam turned by close angles of rotation.

According to the second aspect of the present invention, the first enhancement sharpens projection data items contained in fan-beam data items detected with an X-ray beam turned by close angles of rotation.

According to the third aspect of the present invention, there is provided an X-ray CT image reconstruction method identical to the X-ray CT image reconstruction method according to the second aspect of the invention except that assuming that j denotes a view number indicating an angle of rotation, i denotes a channel number indicating a location where a projection line is terminated, r denotes a row number indicating a location in a thickness direction, $P_{i,j,r}$ denotes a fan-beam data value identified with the view number j, channel number i, and row number r, w denotes a number width that is a range of view numbers j of views to be treated, k denotes a parameter with which a view number of a view to be treated is designated, Wk denotes a weighting coefficient associated with each view number, and $Q_{i,j,r}$ denotes a fan-beam data value identified with the view number j, channel number i, and row number r and subjected to the first enhancement, the first enhancement employs the following formula (1):

$$Q_{i,j,r} = \sum_{k=-W}^{k=W} P_{i,j+k,r} \times W_k \qquad \text{[Formula 1]}$$

According to the fourth aspect of the present invention, there is provided an X-ray CT image reconstruction method identical to the X-ray CT image reconstruction method according to any of the first to third aspects of the present invention except that the enhancement includes the second enhancement of sharpening projection data items contained in a plurality of fan-bean data items detected at locations adjoining in the thickness direction.

According to the fourth aspect of the present invention, the second enhancement sharpens projection data items contained in fan-beam data items detected at locations adjoining in the thickness direction.

According to the fifth aspect of the present invention, there is provided an X-ray CT image reconstruction method identical to the X-ray CT image reconstruction method according to the fourth aspect of the present invention except that: assuming that j denotes a view number indicating an angle of rotation, i denotes a channel number indicating a location where a projection line is terminated, r denotes a row number indicating a location in a thickness direction, $P_{i,j,r}$ denotes a fan-beam data value identified with the view number j, channel number i, and row number r, w denotes a number width that is a range of row numbers r indicating locations in the thickness direction where projection data items to be treated are detected, k denotes a parameter with which a row number indicating a location in the thickness direction where projection data to be treated is detected is designated, $W_k$ denotes a weighting coefficient associated with each row number, and $R_{i,j,r}$ denotes a fan-beam data value identified with the view number j, channel number i, and row number r, the second enhancement employs the following formula (2):

$$R_{i,j,r} = \sum_{k=-W}^{k=W} P_{i,j,r+k} \times W_k \qquad \text{[Formula 2]}$$

According to the sixth aspect of the present invention, there is provided an X-ray CT image reconstruction method in which: a fan-shaped X-ray beam that is thick and irradiated to a subject is turned about the subject; projection data items concerning an X-ray beam transmitted by the subject are detected with the X-ray beam turned by a plurality of successive angles of rotation; fan-beam data including projection data items detected with an X-ray beam turned by the angles of rotation is used to produce parallel-beam data, which has values thereof defined along parallel projection lines, in relation to each angle of projection; the parallel-beam data is enhanced in units of a projection line; and the enhanced parallel-beam data is used to reconstruct an image.

According to the sixth aspect of the present invention, parallel-beam data is enhanced and then used to reconstruct an image.

According to the seventh aspect of the present invention, there is provided an X-ray CT image reconstruction method identical to the X-ray CT image reconstruction method according to the sixth aspect of the present invention except that the enhancement includes the first enhancement of sharpening data items contained in a plurality of parallel-beam data items and defined along projection lines whose angles of projection are close to one another.

According to the seventh invention, the first enhancement sharpens data items contained in parallel-beam data items and defined along projection lines whose angles of projection are close to one another.

According to the eighth aspect of the present invention, there is provided an X-ray CT image reconstruction method identical to the X-ray CT image reconstruction method according to the sixth or seventh aspect of the present invention except that the enhancement includes the second enhancement of sharpening data items contained in a plurality of parallel-beam data items and defined at locations adjoining in a thickness direction.

According to the eighth aspect of the present invention, the second enhancement sharpens data items contained in parallel-beam data items and defined at locations adjoining in the thickness direction.

According to the ninth aspect of the present invention, there is provided an X-ray CT image reconstruction method in which: a fan-shaped X-ray beam that is thick and irradiated to a subject is turned about the subject; projection data items concerning an X-ray beam transmitted by the subject are detected with the X-ray beam turned by a plurality of successive angles of rotation; fan-beam data including projection data items detected with an X-ray beam turned by the angles of rotation is used to produce parallel-beam data, which has values thereof defined along parallel projection lines, in relation to each angle of projection; the parallel-beam data is used to reconstruct an image of the subject represented by tomographic image data; a point associated with a scan center position equivalent to a rotation center position is identified in the image represented by the tomographic image data; and the third enhancement is performed in order to sharpen pixels constituting the tomographic image data so that a pixel whose distance from the point associated with the scan center position is longer will be sharpened to a greater degree.

According to the ninth aspect of the present invention, the third enhancement of tomographic image data is such that a pixel whose distance from the point associated with the scan center position is longer is sharpened to a greater degree.

According to the tenth aspect of the present invention, there is provided an X-ray CT image reconstruction method in which: a fan-shaped X-ray beam that is thick and irradiated to a subject is turned about the subject; projection data items concerning an X-ray beam transmitted by the subject are detected with the X-ray beam turned by a plurality of successive angles of rotation; local transmissible region data concerning X-rays transmitted by a local region of the subject is sampled from fan-beam data including projection data items detected with an X-ray beam turned by the angles of rotation; the local transmissible region data is Fourier-transformed in order to produce local frequency-domain data; after high-pass filtering is performed in order to remove a low-frequency component from the local frequency-domain data, the local frequency-domain data having undergone high-pass filtering is inverse-Fourier-transformed in order to produce sharpened local transmissible region data; the sharpened local transmissible region data concerning X-rays irradiated at the angles of rotation along projection lines that fan out is used to produce parallel-beam data, which has values thereof defined along parallel projection lines, in relation to each angle of projection; and the parallel-beam data is used to reconstruct an image.

According to the tenth aspect of the present invention, high-pass filtering removes a low-frequency component from the local frequency-domain data resulting from Fourier transform of fan-beam data, and sharpens the original local transmissible region data.

According to the eleventh aspect of the present invention, there is provided an X-ray CT image reconstruction method in which: a fan-shaped X-ray beam that is thick and irradiated to a subject is turned about the subject; projection data items concerning an X-ray beam transmitted by the subject are detected with the X-ray beam turned by a plurality of successive angles of rotation; fan-beam data including projection data items detected with an X-ray beam turned by the angles of rotation is used to produce parallel-beam data, which has values thereof defined along parallel projection lines, in relation to each angle of projection; local transmissible region data concerning X-rays transmitted by a local region of the subject is sampled from the parallel-beam data; the local transmissible region data is Fourier-transformed in order to produce local frequency-domain data; after high-pass filtering is performed in order to remove a low-frequency component from the local frequency-domain data, the local frequency-domain data having undergone the high-pass filtering is inverse-Fourier-transformed in order to produce sharpened local transmissible region data; and the sharpened local transmissible region data is used to reconstruct an image.

According to the eleventh aspect of the present invention, the high-pass filtering removes a low-frequency component from local frequency-domain data resulting from Fourier transform of parallel-beam data, to sharpen original local transmissible region data.

According to the twelfth aspect of the present invention, there is provided an X-ray CT system comprising: a rotator that turns a fan-shaped X-ray beam, which is thick and irradiated to a subject, about the subject; an X-ray detector that detects projection data items concerning an X-ray beam, which is transmitted by the subject, with the X-ray beam turned by a plurality of successive angles of rotation; an enhancement means for performing the first enhancement on fan-beam data, which includes projection data items detected with an X-ray beam turned by the angles of rotation, so as to sharpen projection data contained in the fan-beam data and acquired along each projection line; a projection line conversion means for producing parallel-beam data, which has values thereof defined along parallel projection lines, in relation to each angle of projection using the enhanced fan-beam data; and an image reconstruction means for reconstructing an image using the parallel-beam data.

According to the thirteenth aspect of the present invention, there is provided an X-ray CT system identical to the X-ray CT system according to the twelfth aspect of the present invention except that the enhancement means includes a first enhancement means for performing the first enhancement so as to sharpen projection data items contained in a plurality of fan-beam data items detected with an X-ray beam turned by close angles of rotation.

According to the fourteenth aspect of the present invention, there is provided an X-ray CT system identical to the X-ray CT system according to the twelfth or thirteenth aspect of the present invention except that the enhancement means includes a second enhancement means for performing the second enhancement so as to sharpen projection data items contained in a plurality of fan-beam data items detected at locations adjoining in a depth direction.

According to the fifteenth aspect of the present invention, there is provided an X-ray CT system comprising: a rotator that turns a fan-shaped X-ray beam, which is thick and irradiated to a subject, about the subject; an X-ray detector that detects projection data items concerning an X-ray beam, which is transmitted by the subject, with the X-ray beam turned by a plurality of successive angles of rotation; a projection line conversion means for producing parallel-beam data, which has values thereof defined along parallel projection lines, in relation to each angle of projection using fan-beam data that includes projection data items detected with an X-ray beam turned by the angles of rotation; an enhancement means for enhancing the parallel-beam data so as to sharpen data contained in the parallel-beam data and defined along each projection line; and an image reconstruction means for reconstructing an image using the enhanced parallel-beam data.

According to the sixteenth aspect of the present invention, there is provided an X-ray CT system identical to the X-ray CT system according to the fifteenth aspect of the present invention except that the enhancement means includes a first enhancement means for performing the first enhancement so as to sharpen data items contained in a plurality of parallel-beam data items and defined along projection lines whose angles of projection are close to one another.

According to the seventeenth aspect of the present invention, there is provided an X-ray CT system identical to the X-ray CT system according to the fifteenth or sixteenth aspect of the present invention except that the enhancement means includes a second enhancement means for performing the second enhancement so as to sharpen data items contained in a plurality of parallel-beam data items and defined at locations adjoining in a depth direction.

According to the eighteenth aspect of the present invention, there is provided an X-ray CT system comprising: a rotator that turns a fan-shaped X-ray beam, which is thick and irradiated to a subject, about the subject; an X-ray detector that detects projection data items concerning an X-ray beam, which is transmitted by the subject, with the X-ray beam turned by a plurality of successive angles of rotation; a projection line conversion means for producing parallel-beam data, which has values thereof defined along parallel projection lines, in relation to each angle of projection using fan-beam data that includes projection data items detected with an X-ray beam turned by the angles of rotation; an image reconstruction means for reconstructing an image of the subject, which is represented by tomographic image data, using the parallel-beam data; and a third enhancement means for identifying a point in an image, which is represented by the tomographic image data, associated with a scan center position equivalent to a rotation center position, and sharpening pixels, which constitute the tomographic image data, so that a pixel whose distance from the point associated with the scan center position is longer will be sharpened to a greater degree.

According to the nineteenth aspect of the present invention, there is provided an X-ray CT system comprising: a rotator that turns a fan-shaped X-ray beam, which is thick and irradiated to a subject, about the subject; an X-ray detector that detects projection data items concerning an X-ray beam, which is transmitted by the subject, with the X-ray beam turned by a plurality of successive angles of rotation; a local region sampling means for sampling local transmissible region data concerning an X-ray beam, which is transmitted by a local region of the subject, from fan-beam data including projection data items detected with an X-ray beam turned by the angles of rotation; a fourth enhancement means for Fourier-transforming the local transmissible region data so as to produce local frequency-domain data, and for, after performing high-pass filtering so as to remove a low-frequency component from the local frequency-domain data, inverse-Fourier-transforming the local frequency-domain data having undergone the high-pass filtering so as to produce sharpened local transmissible region data; a projection line conversion means for producing parallel-beam data, which has values thereof defined along parallel projection lines, in relation to each angle of projection using the sharpened local transmissible region data; and an image reconstruction means for reconstructing an image using the parallel-beam data.

According to the twentieth aspect of the present invention, there is provided an X-ray CT system comprising: a rotator that turns a fan-shaped X-ray beam, which is thick and irradiated to a subject, about the subject; an X-ray detector that detects projection data items concerning an X-ray beam, which is transmitted by the subject, with the X-ray beam turned by a plurality of successive angles of rotation; a projection line conversion means for producing parallel-beam data, which has values thereof defined along parallel lines, in relation to each angle of projection using fan-beam data that includes projection data items detected with an X-ray beam turned by the angles of rotation; a local region sampling means for sampling local transmissible region data concerning an X-ray beam, which is transmitted by a local region of the subject, from the parallel-beam data; a fourth enhancement means for Fourier-transforming the local transmissible region data so as to produce local frequency-domain data, and for, after performing high-pass filtering so as to remove a low-frequency component from the local frequency-domain data, inverse-Fourier-transforming the local frequency-domain data having undergone high-pass filtering so as to produce sharpened local transmissible region data; and an image reconstruction means for reconstructing an image of the subject, which is represented by local tomographic image data, using the sharpened local transmissible region data.

As mentioned above, according to the present invention, any of the first to fourth enhancements is performed in order to sharpen fan-beam data, parallel-beam data, or tomographic image data. Consequently, striped artifacts derived from conversion from fan-beam data into parallel-beam data according to the MIP method are minimized. A decrease in a resolution of a tomographic image occurring at a point in the image far away from a point associated with a scan center position can be alleviated. In particular, the image quality of a tomographic image of the delicate lung field at a point in the image away from the point associated with the scan center position can be improved.

Further objects and advantages of the present invention will be apparent from the following description of the preferred embodiments of the invention as illustrated in the accompanying drawings.

BRIEF DESCRIPTION OF THE DRAWINGS

FIG. 13 is a flowchart describing actions to be performed during the fourth enhancement according to the fourth embodiment.

DETAILED DESCRIPTION OF THE INVENTION

Referring to the appended drawings, the best mode for implementing an X-ray CT image reconstruction method and an X-ray CT system in accordance with the present invention will be described below. Noted is that the present invention will not be limited to the best mode.

FIRST EMBODIMENT

Figure 1:
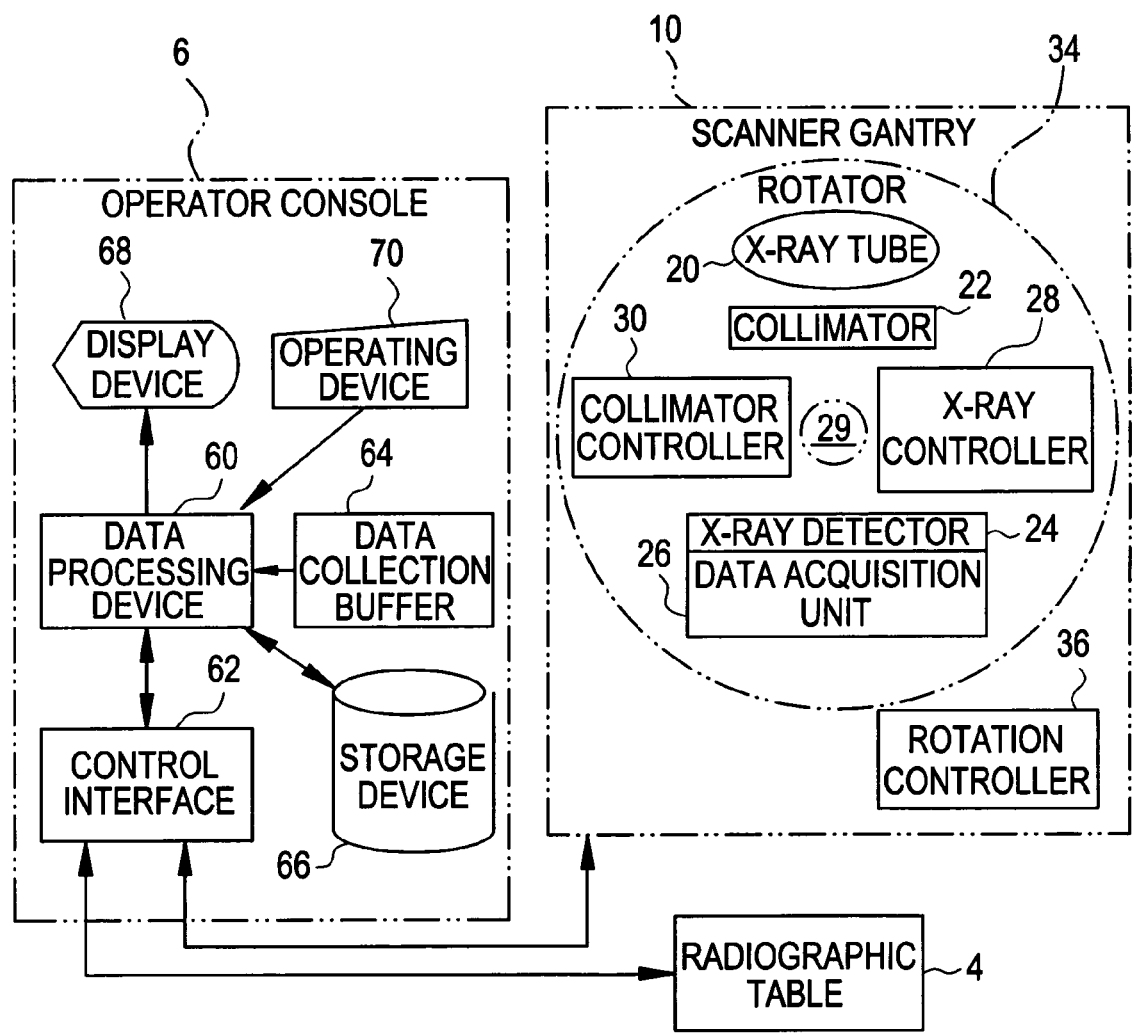
FIG. 1 is a block diagram showing the overall configuration of an X-ray CT system.

To begin with, the overall configuration of an X-ray CT system according to the first embodiment will be described below. FIG. 1 is a block diagram showing the X-ray CT system. As shown in FIG. 1, the X-ray CT system includes a scanner gantry 10 and an operator console 6.

The scanner gantry 10 includes an X-ray tube 20. X-rays that are not shown but are radiated from the X-ray tube 20 are reshaped into a conical X-ray beam, which fans out and is thick, by a collimator 22, and are irradiated into an X-ray detector 24.

The X-ray detector 24 has a plurality of scintillators set in array in the form of a matrix in a direction in which the fan-beam X-rays spread. The X-ray detector 24 is a multi-channel detector that is wide to have the plurality of scintillators set in array in the form of a matrix.

The X-ray detector 24 offers an X-ray incidence surface, which is curved in a concave manner, as a whole. The X-ray detector 24 is a combination of scintillators made of an inorganic crystal and photodiodes serving as photoelectric converters.

A data acquisition unit 26 is connected to the X-ray detector 24. The data acquisition unit 26 acquires information detected by each of the scintillators included in the X-ray detector 24. An X-ray controller 28 controls X-irradiation from the X-ray tube 20. The connective relationship between the X-ray tube 20 and the X-ray controller 28 and the connective relationship between the collimator 22 and a collimator controller 30 are not shown. The collimator 22 is controlled by the collimator controller 30.

The foregoing components starting with the X-ray tube 20 and ending with the collimator controller 30 are incorporated in a rotator 34 included in the scanner gantry 20. Herein, a subject or a phantom lies down on a radiographic table 4 in a bore 29 located in the center of the rotator 34. The rotator 34 is controlled to rotate by a rotation controller 36. The X-ray 20 bombards X-rays, and the X-ray detector 24 detects X-rays transmitted by the subject or phantom in the form of projection data items constituting each view according to an angle of rotation by which the scanner gantry is rotated. The connective relationship between the rotator 34 and the rotation controller 36 is not shown in any drawing.

The operator console 6 includes a data processing device 60. The data processing device 60 includes, for example, a computer and further includes a preprocessing means, first to fourth pieces of enhancement means, an image reconstruction means, and a post-processing means. A control interface 62 is connected to the data processing device 60. The scanner gantry 10 is connected to the control interface 62. The data processing device 60 controls the scanner gantry 10 via the control interface 62.

The data acquisition unit 26, X-ray controller 28, collimator controller 30, and rotation controller 36 incorporated in the scanner gantry 10 are controlled via the control interface 62. The connections of the control interface 62 to these components are not shown in any drawing.

A data collection buffer 64 is connected to the data processing device 60. The data collection buffer 64 is connected to the data acquisition unit 26 incorporated in the scanner gantry 10. Data acquired by the data acquisition unit 26 is transferred to the data processing device 60 via the data collection buffer 64.

The data processing device 60 reconstructs images using a transmitted X-ray signal, that is, projection data items acquired via the data collection buffer 64. Moreover, a storage device 66 is connected to the data processing device 60. Projection data items collected into the data collection buffer 64, reconstructed tomographic image data items, and programs that implement the capabilities of the X-ray CT system are stored in the storage device 66.

A display device 68 and an operating device 70 are connected to the data processing device 60. Tomographic images and other information sent from the data processing device 60 are displayed on the display device 68. The operating device 70 is manipulated by an operator and transfers various instructions and pieces of information to the data processing device 60. The operator uses the display device 68 and operating device 70 to interactively operate the X-ray CT system. The scanner gantry 10, radiographic table 4, and operator console 6 radiograph a subject or a phantom so as to acquire tomographic image data items.

Figure 2:
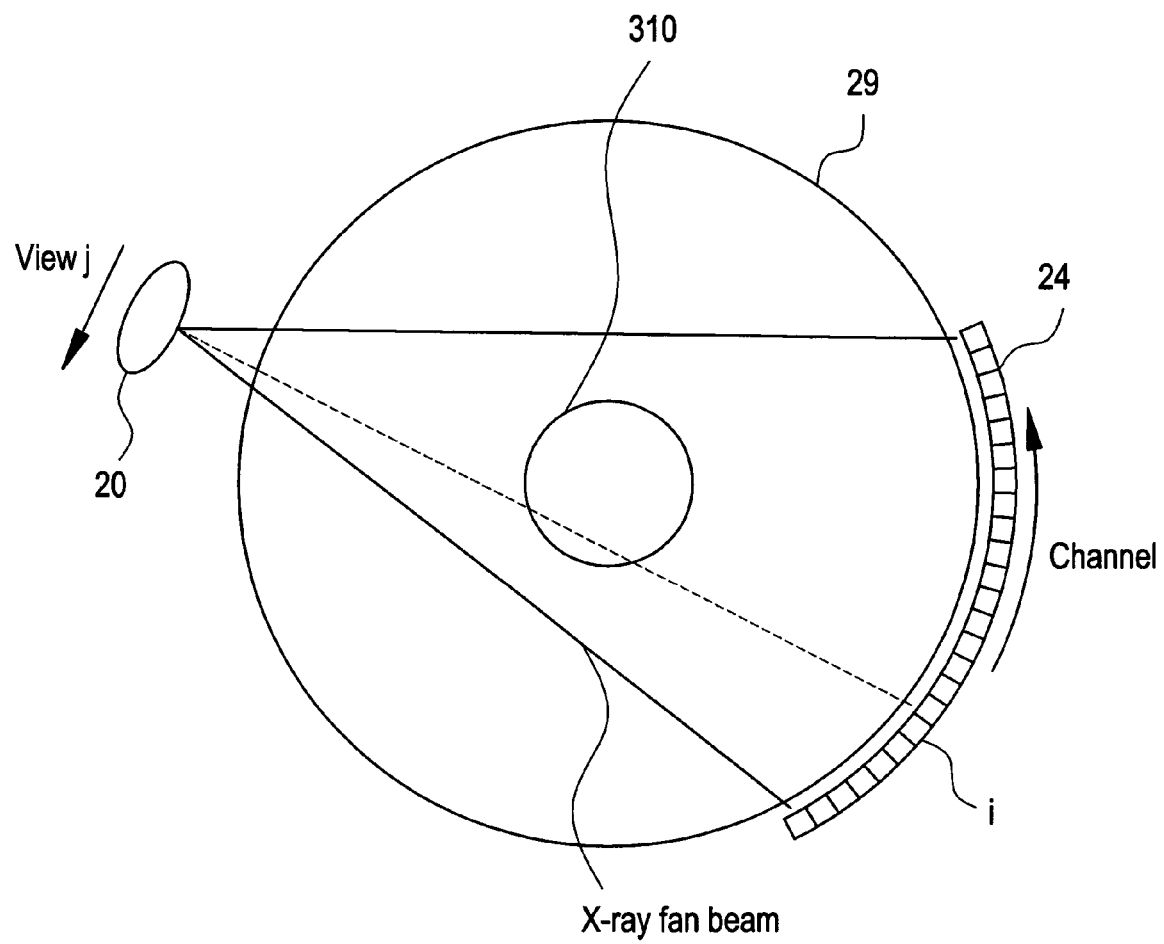
FIG. 2 is an explanatory diagram showing radiography to be performed by an X-ray tube and an X-ray detector.

FIG. 2 shows the X-ray tube 20, the X-ray detector 24, and a phantom 310 disposed in the bore 29. The phantom 310 has a circular section and has the center thereof aligned with a radiographic center in the bore 29. An X-ray fan beam radiated from the X-ray tube 20 is transmitted by the phantom 310 and detected by the X-ray detector 24.

The X-ray detector 24 has a plurality of scintillators set in array in a direction in which an X-ray fan beam fans out, and detects projection data of the phantom 310 on each channel identified with a channel number. Herein, the X-ray tube 20, collimator 21, and X-ray detector 24 are opposed to one another with the bore 29 as a center, and rotated about the bore 29 with the relative positions thereof held unchanged in order to acquire projection data. Projection data items constituting each view identified with a view number j indicating an angle of rotation are acquired in order to produce fan-beam data including views. The X-ray fan beam has a thickness in a depth direction of the bore 29 orthogonal to a plane of rotation on which the rotator 34 rotates. The X-ray detector 24 that detects the X-ray fan beam has the plurality of arrays of scintillators extended in the thickness direction, and detects projection data items at each of arrays of scintillators lined in the thickness direction which is identified with a row number r similarly to with the view number j.

Figure 3A:
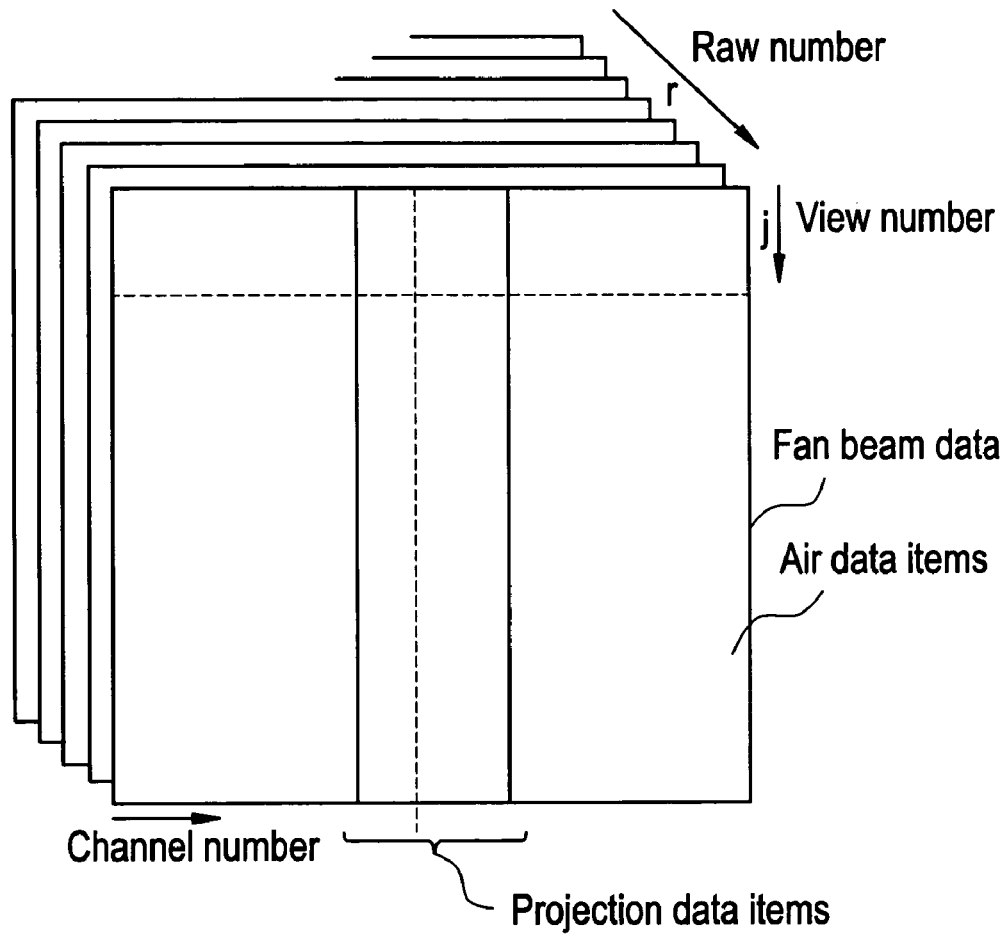
FIGS. 3a and 3b are exemplary diagrams showing fan-beam data items acquired by the X-ray CT system.

FIG. 3 illustratively shows projection data items collected into the data collection buffer 64, and a plurality of fan-beam data items produced from the projection data items. FIG. 3(A) shows the fan-beam data items each of which is acquired by rotating the X-ray tube 20 and X-ray detector 24 incorporated in the rotator 34 by one turn about the phantom 310. The fan-beam data is two-dimensional data defined with respect to two axes of coordinates one of which reads the view number j indicating an angle of rotation by which the rotator 34 is rotated and the other of which reads the channel number i indicating the location of a channel. The number of fan-beam data items corresponds to the number of arrays of scintillators juxtaposed in the thickness direction, that is, the number of fan-beam data items corresponds to the number of locations juxtaposed in the thickness direction and indicated with row numbers r.

Figure 3B:
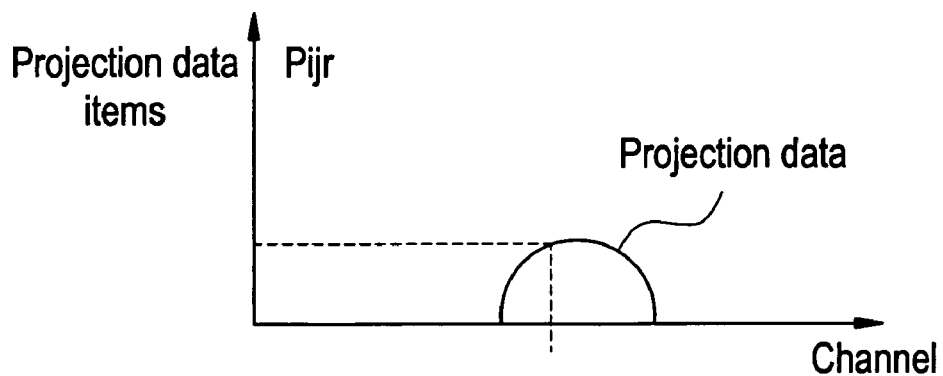

FIG. 3(B) shows an example of projection data items identified with a view number j and a row number r. In FIG. 3(B), the axis of abscissas reads a channel number and the axis of ordinates reads a fan-beam data value $P_{i,j,r}$. Projection data items concerning the phantom 310 are plotted in relation to a central channel number and nearby channel numbers. Channel numbers in relation to which no projection data is plotted indicate channels to which X-rays having passed through a space in the bore 29 in which only air is present are irradiated.

Figure 4:
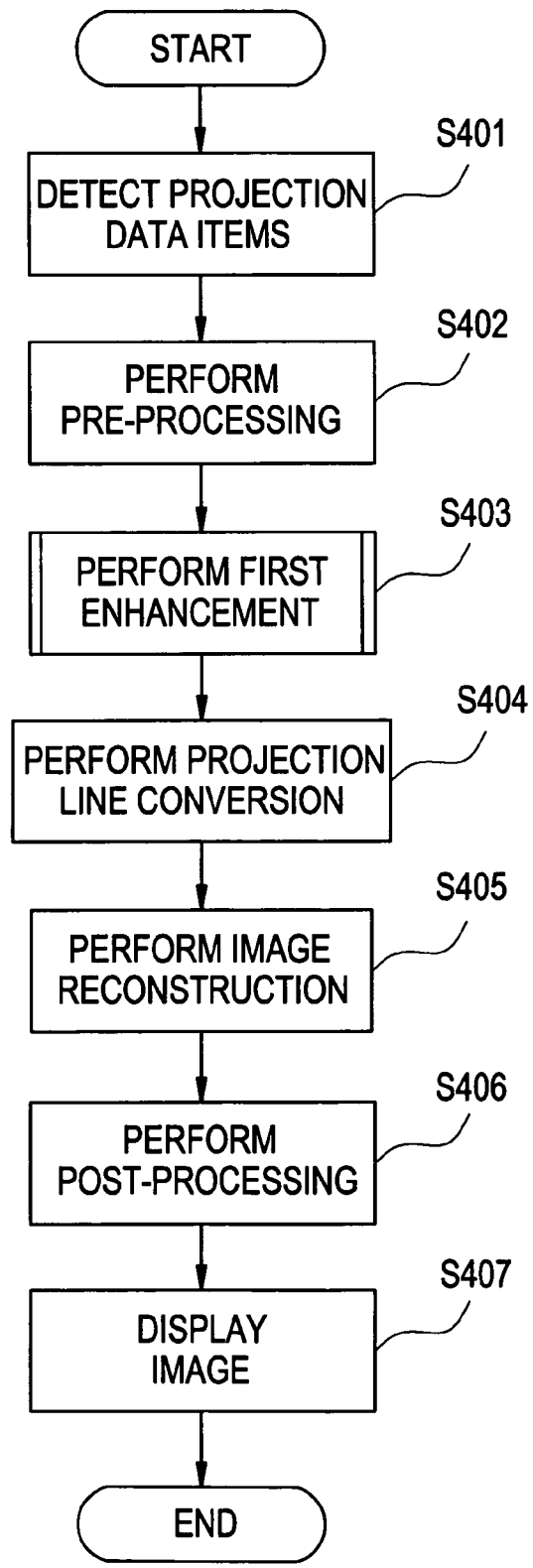
FIG. 4 is a flowchart describing actions to be performed by a data processing device included in the first embodiment.

Actions to be performed by the data processing device 60 according to the first embodiment will be described in conjunction with FIG. 4. FIG. 4 is a flowchart describing the actions to be performed by the data processing device 60. First, an operator moves a subject lying down on the radiographic table 4 to the center of the bore 29, and acquires projection data items concerning the subject in units of a view number j indicating an angle of rotation by which the rotator 34 is rotated (step S401). Consequently, fan-beam data having projection data items arranged in order of the view number as shown in FIG. 3(A) is collected into the data collection buffer 64. At the same time, a plurality of fan-beam data items detected at the locations in the thickness direction indicated with respective row numbers is acquired.

Thereafter, the data processing device 60 performs preprocessing on the fan-beam data collected in the data collection buffer 64 (step S402). The preprocessing includes compensation of an offset of fan-beam data, logarithmic conversion, X-ray dose correction, and X-ray detector sensitivity correction. Moreover, a variation in the intensity of X-rays radiated by the X-ray tube 20 or a variance in the sensitivity of the X-ray detector 24 is compensated.

Figure 5:
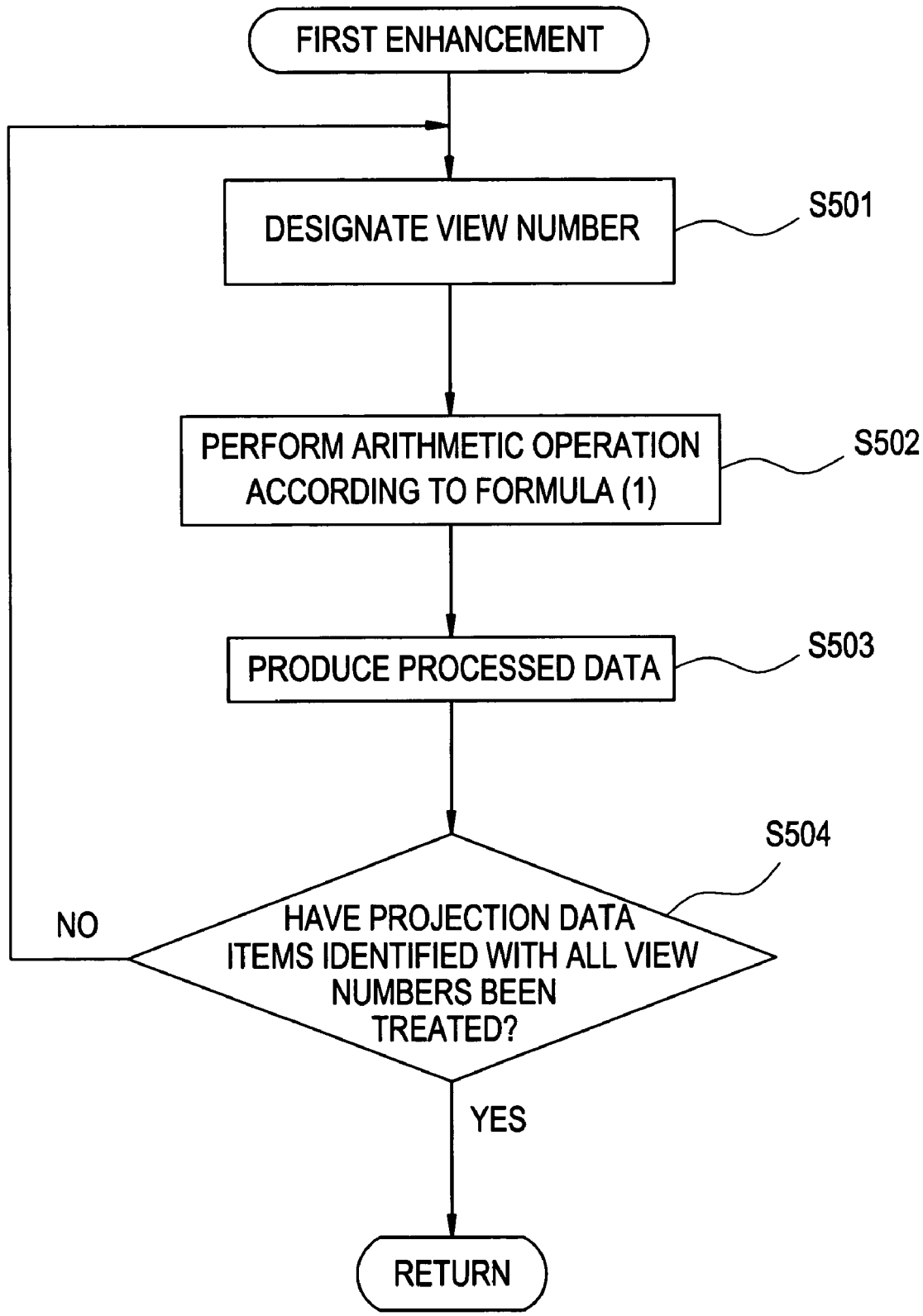
FIG. 5 is a flowchart describing actions to be performed during the first enhancement.

Thereafter, the first enhancement means included in the data processing device 60 performs the first enhancement on projection data items identified with each view number (step S403). FIG. 5 is a flowchart describing actions to be performed during the first enhancement. The first enhancement means designates a view number j (step S501). The view number is counted up from 1. Every time the view number is updated, the view number is incremented by one and designated as the next view number.

Thereafter, the first enhancement means performs an arithmetic operation on projection data items identified with the view number j (step S502). The arithmetic operation is expressed with the following formula (1):

$$Q_{i,j,r} = \sum_{k=-W}^{k=W} P_{i,j+k,r} \times W_k \qquad \text{[Formula 3]}$$

where i denotes a channel number indicating a location where projection data is detected, r denotes a row number indicating a location in a thickness direction, Pi,j,r denotes projection data identified with the view number j, channel number i, and row number r, w denotes a number width that is a range of view numbers of views to be computed, k denotes a parameter with which a view number of a view to be computed is designated, Wk denotes a weighting coefficient assigned to each projection data, and Qi,j,r denotes projection data that is identified with the view number j, channel number i, and row number r and that has undergone the first enhancement.

Figure 6:
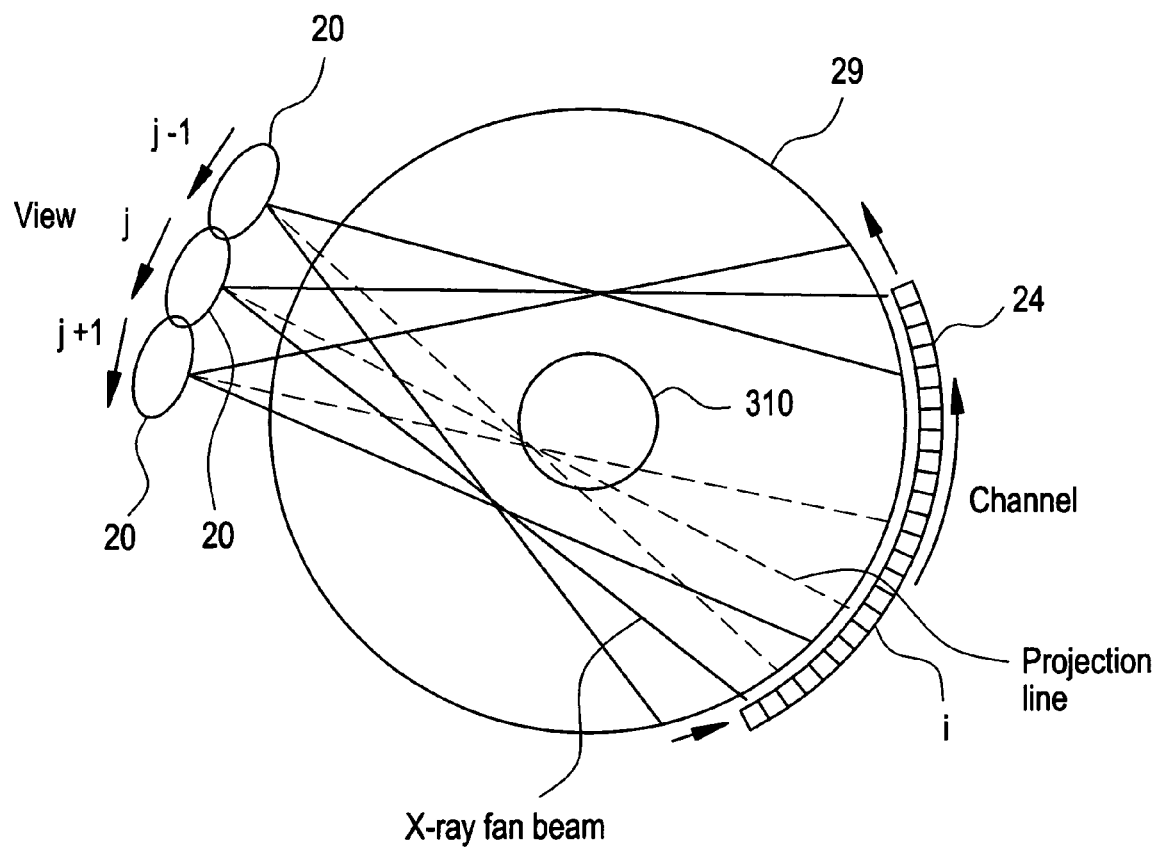
FIG. 6 is an explanatory diagram concerning the first enhancement.

FIG. 6 shows the relationship among views to be computed in terms of an imaged position on the assumption that the number width w is set to 1. Assuming that projection data to be subjected to the first enhancement is identified with a view number j and a channel number i, projection data items identified with view numbers j−1 and j+1 and the channel number i are computed. Herein, angles of rotation at which the projection data items identified with the view numbers j−1 and j+1 are detected are adjacent to an angle of rotation at which projection data identified with the view number j is detected. Consequently, time instants at which the respective projection data items are detected are successive ones. Moreover, a projection line along which the projection data identified with the view number j and channel number i is acquired is indicated with a dashed line in FIG. 6, and is adjacent to projection lines along with the projection data items identified with the view numbers j−1 and j+1 are acquired. Moreover, the time instants at which the respective projection data items are detected are close to one another.

Figure 7:
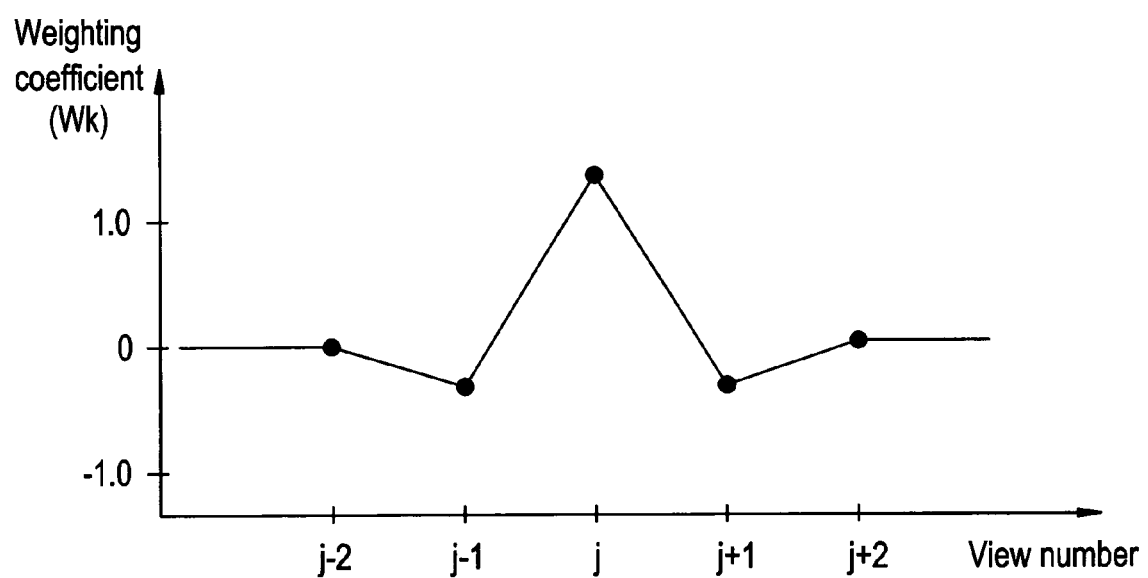
FIG. 7 is an explanatory diagram concerning a weighting coefficient adopted for the first enhancement.

FIG. 7 graphically shows an example of a weighting coefficient $W_k$ assigned to each projection data. In FIG. 7, the axis of ordinates reads the weighting coefficient $W_k$, and the axis of abscissas reads a view number. Herein, the weighting coefficient $W_k$ associated with the view number j with which projection data to be enhanced is identified is a positive value exceeding 1.0, and the weighting coefficients $W_{j+1}$ and $W_{j-1}$ associated with the adjoining view numbers j−1 and j+1 are negative values of decimal fractions. Since the number width w is 1, the weighting coefficients associated with the other view numbers are set to zero.

The weighting coefficient $W_k$ employed in the first enhancement corresponds to what is called a high-pass filter or a differential filter employed in spatial filtering, and sharpens projection data items contained in views and detected at successive time instants.

Referring back to FIG. 5, the first enhancement means produces processed data $Q_{i,j,r}$ from projection data identified with the view number j (step S503). The first enhancement means checks projection data items identified with all view numbers to see if the first enhancement is performed on the projection data items (step S504). If the first enhancement has not been performed on the projection data items identified with all the view numbers (in the negative at step S504), control is passed to step S501. After the view number is updated, an arithmetic operation is performed again. If the first enhancement has been performed on the projection data items identified with all the view numbers (in the affirmative at step S504), the first enhancement is terminated.

Referring back to FIG. 4, the data processing device 60 performs projection line conversion so as to convert fan-beam data, which has undergone the first enhancement, into parallel-beam data (step S404). During the projection line conversion, as shown in FIG. 2 and FIG. 3, an X-ray fan beam is detected, and fan-beam data having projection data items arranged in order of the view number is converted into parallel-beam data having values thereof defined along parallel projection lines that share the same angle of projection (refer to, for example, Patent Document 1). Owing to the projection line conversion, after image reconstruction to be described later is completed, if image processing is performed according to an MIP method or the like, striped artifacts derived from the image processing can be minimized.

Thereafter, the image reconstruction means included in the data processing device 60 performs image reconstruction on parallel-beam data (step S405). The image reconstruction means performs image reconstruction on the parallel-beam data according to a filtered back projection (FBR) method or the like so as to produce tomographic image data (refer to, for example, Non-patent Document 2).

Thereafter, the data processing device 60 performs post-processing such as CT number conversion on the tomographic image data (step S406). An image is then displayed according to the tomographic image data (step S407). The processing is terminated.

Figure 8:
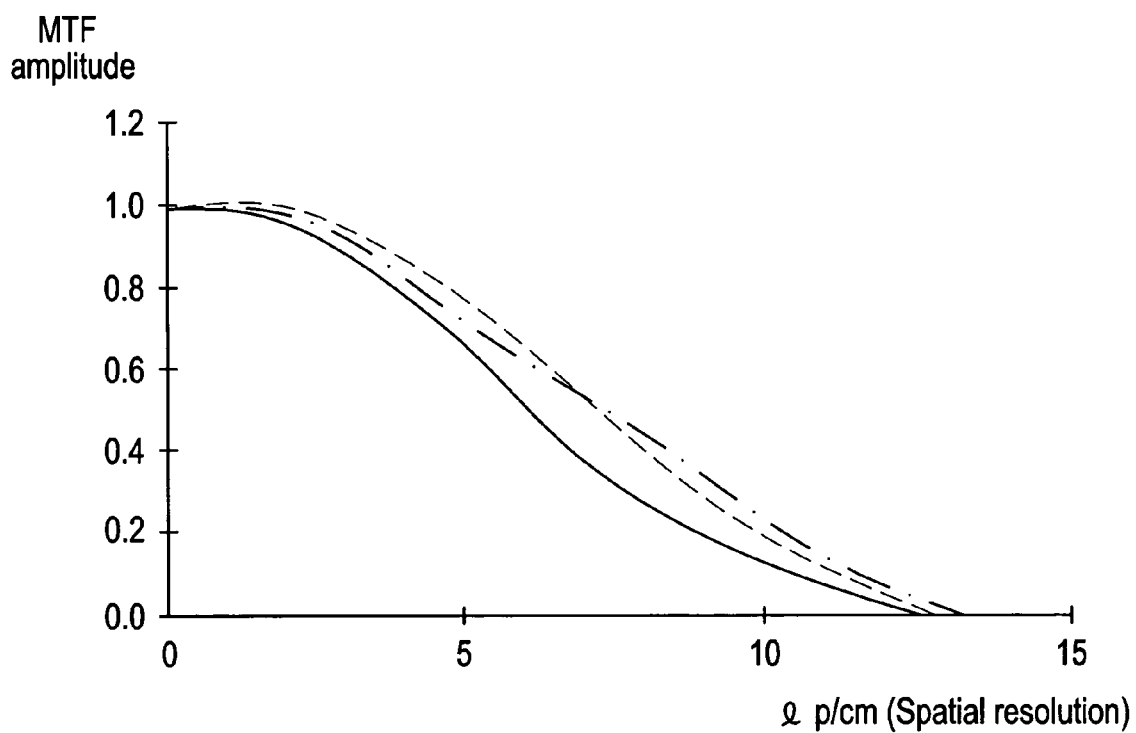
FIG. 8 shows MTF graphs plotted with values actually measured from reconstructed images according to the first embodiment.

FIG. 8 graphically shows a degree of improvement in the quality of tomographic images derived from the first enhancement by actually measuring a modulation transfer function (MTF). The MTF shown in FIG. 8 is measured with a wire phantom placed at a position separated by 7 cm from a scan center position.

In FIG. 8, the axis of ordinates reads an amplitude, and the axis of abscissas reads the number of black and while line pairs per unit length (lines per mm) that is used as an index of a spatial resolution. Herein, the larger the number of black and white line pairs indicated on the axis of abscissas is, that is, the higher the spatial resolution is, the smaller the amplitude indicated on the axis of ordinates is. In other words, a resolution decreases. Namely, the smaller the decrease is, the higher the resolution is.

In FIG. 8, a solid line expresses an MTF graph plotted with values actually measured from image data reconstructed using parallel-beam data that results from processing which is performed by the data processing device 60 as described in FIG. 4 and from which the first enhancement of step S403 is excluded. Moreover, a dot-dash line in FIG. 8 expresses an MTF graph plotted with values actually measured from image data reconstructed using fan-beam data that results from the processing which is performed by the data processing device 60 as described in FIG. 4 and from which the first enhancement of step S403 and the projection line conversion of step S404 are excluded. A dotted line in FIG. 8 expresses an MTF graph plotted with values actually measured from image data reconstructed using parallel-beam data that results from the processing which is performed by the data processing device 60 as described in FIG. 4 and which includes the first enhancement.

In any of the MTF graphs expressed with the solid line, dot-dash line, and dotted line in FIG. 8, the amplitude decreases along with an increase in the spatial resolution indicated on the axis of abscissas. However, in case parallel-beam data that has not undergone the first enhancement is employed, the decrease in the amplitude and the decrease in the spatial resolution are, as shown in the MTF graph expressed with the solid line, markedly large. On the other hand, in case parallel-beam data having undergone the first enhancement is employed, the decrease in the amplitude is, as shown with the MTF graph expressed with the dotted line, limited. The decrease in the spatial resolution is substantially equal to the decrease therein occurring when fan-beam data is employed. Incidentally, the employment of parallel-beam data minimizes striped artifacts derived from the MIP method.

As mentioned above, according to the first embodiment, projection line conversion is performed in order to convert fan-beam data into parallel-beam data. Prior to the projection line conversion, the first enhancement is performed on projection data items contained in views detected at mutually close time instants. Consequently, a variance among time instants, at which projection data items are detected, occurring when fan-beam data is converted into parallel-beam data can be alleviated. Moreover, striped artifacts occurring during implementation of the MIP method and deriving from the projection line conversion can be minimized. Furthermore, a decrease in a resolution occurring at a point in an image far away from a point associated with a scan center position can be reduced.

According to the first embodiment, the first enhancement of step S403 is succeeded by the projection line conversion of step S404. Alternatively, the first enhancement may be performed on parallel-beam data resulting from the projection line conversion.

According to the first embodiment, fan-beam data like the one shown in FIG. 3 is employed. The fan-beam data may be produced by performing either conventional scanning or helical scanning. As far as tomographic images resulting especially from helical scanning are concerned, since a marked decrease in a resolution occurs in part of a tomographic image showing the lung field and its surroundings, the first embodiment is highly advantageous.

SECOND EMBODIMENT

According to the first embodiment, the first enhancement is performed on views contained in fan-bean data. Alternatively, the second enhancement may be performed on a plurality of fan-beam data items detected at locations in a depth direction. According to the second embodiment, the second enhancement is performed on fan-beam data items identified with different row numbers that are successive in the depth direction.

A hardware configuration and acquired data items employed in the second embodiment of the present invention are identical to those shown in FIG. 1 to FIG. 3. An iterative description will therefore be omitted. Moreover, a flowchart describing actions to be performed by the data processing device 60 is identical to that of FIG. 4 except that the second enhancement is substituted for the first enhancement at step S403. The iterative description of the actions will be omitted, but only the second enhancement to be performed at step S403 will be described below.

Figure 9:
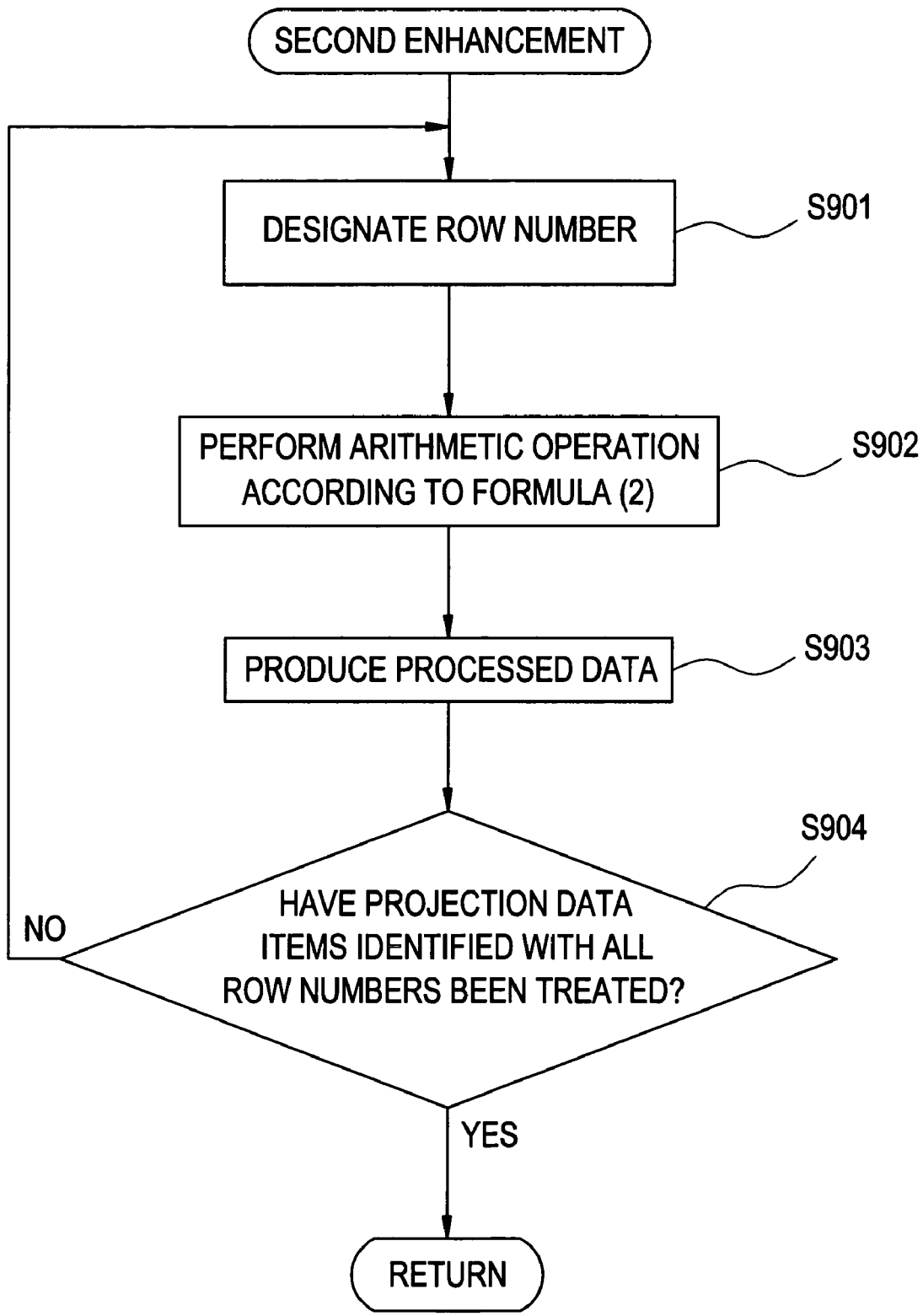
FIG. 9 is a flowchart describing actions to be performed during the second enhancement according to the second embodiment.

FIG. 9 is a flowchart describing actions to be performed during the second enhancement employed in the second embodiment. The second enhancement means included in the data processing device 60 designates a row number r that corresponds to a number indicating a location of fan-beam data in a depth direction (step S901). The row number is counted up from 1. Every time the row number is updated, the row number is incremented by one and designated as the next row number.

Thereafter, the second enhancement means performs an arithmetic operation on the fan-beam data identified with the row number r (step S902). The arithmetic operation is expressed with the following formula (2):

$$R_{i,j,r} = \sum_{k=-W}^{k=W} P_{i,j,r+k} \times W_k \qquad \text{[Formula 4]}$$

where i denotes a channel number indicating a location where projection data is detected, r denotes a row number, $P_{i,j,r}$ denotes projection data identified with a view number j, the channel number i, and the row number r, w denotes a number width that is a range of row numbers indicating locations of fan-beam data items containing projection data items to be treated with the arithmetic operation, k denotes a parameter with which a row number indicating a location of fan-beam data containing projection data to be treated is identified (S903), $W_k$ denotes a weighting coefficient assigned to each projection data, and $R_{i,j,r}$ denotes projection data that is identified with the view number j, channel number i, and row number r and that has undergone the second enhancement (S904).

Figure 10:
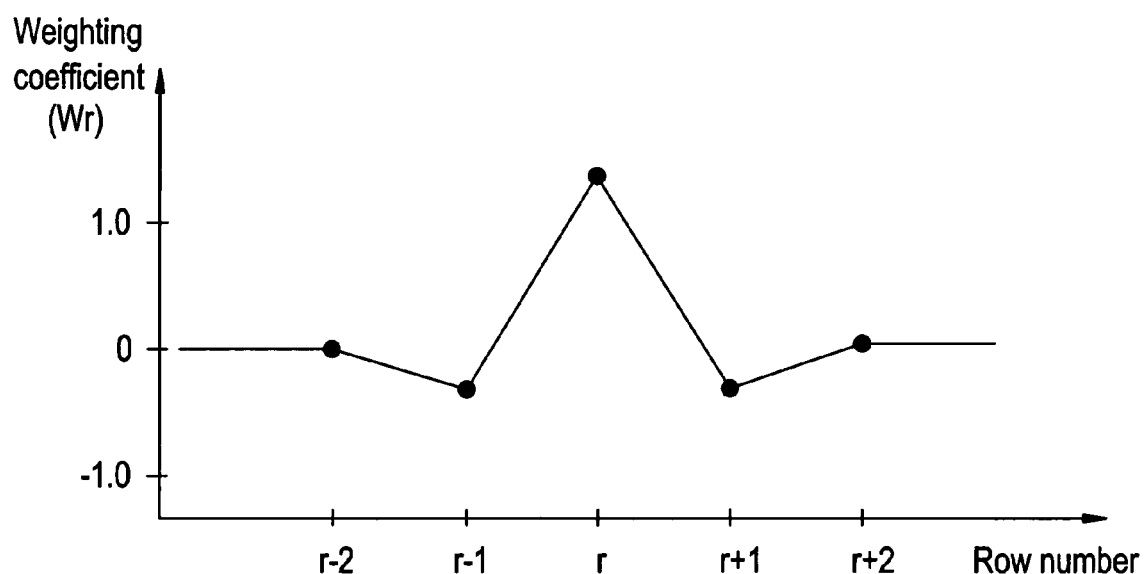
FIG. 10 is an explanatory diagram showing a weighting coefficient adopted for the second enhancement.

FIG. 10 shows an example of the weighting coefficient $W_k$ assigned to each projection data on the assumption that the number width w is set to 1. In FIG. 10, the axis of ordinates reads the weighting coefficient $W_k$, and the axis of abscissas reads the row number. Herein, the weighting coefficient $W_k$ associated with the row number r indicating a location of fan-beam data containing projection data on which the second enhancement is performed is a positive value exceeding 1.0. The weighting coefficients $W_{k+1}$ and $W_{k-1}$ associated with adjoining row numbers k−1 and k+1 are negative values of decimal fractions. Since the number width is set to 1, the weighting coefficients associated with the other row numbers are set to zero.

The second enhancement corresponds to what is called a high-pass filter or a differential filter employed in spatial filtering, and sharpens projection data items contained in fan-beam data items that are detected at the same time instant at locations adjoining in the depth direction and being indicated with adjoining row numbers.

As mentioned above, according to the second embodiment, the second enhancement is performed on projection data items, which are identified with row numbers indicating adjoining locations in the depth direction, instead of the first enhancement described at step S403 in FIG. 4. Since fan-beam data is thus enhanced, a decrease in a resolution derived from conversion of fan-beam data into parallel-beam data can be minimized.

Moreover, according to the second embodiment, the second enhancement is performed on projection data items identified with row numbers prior to the projection line conversion of step S404. Alternatively, the second enhancement may be performed on parallel-beam data resulting from the projection line conversion.

THIRD EMBODIMENT

According to the first and second embodiments, the first or second enhancement is performed on projection data items contained in fan-beam data and identified with view numbers or row numbers in order to minimize a decrease in a resolution occurring in a reconstructed tomographic image. Alternatively, after image reconstruction is completed, the third enhancement may be performed in order to sharpen pixels so that a pixel in an image whose distance from a pixel associated with a scan center position is longer will be sharpened to a greater degree. Thus, the decrease in a resolution occurring in a perimetric part of an image may be reduced. According to the third embodiment, the third enhancement of sharpening pixels in reconstructed image data so that a pixel whose distance from a pixel associated with a scan center position is longer will be sharpened to a greater degree is performed after completion of image reconstruction.

A hardware configuration and acquired data items employed in the third embodiment of the present invention are identical to those shown in FIG. 1 to FIG. 3. An iterative description will therefore be omitted.

Figure 11:
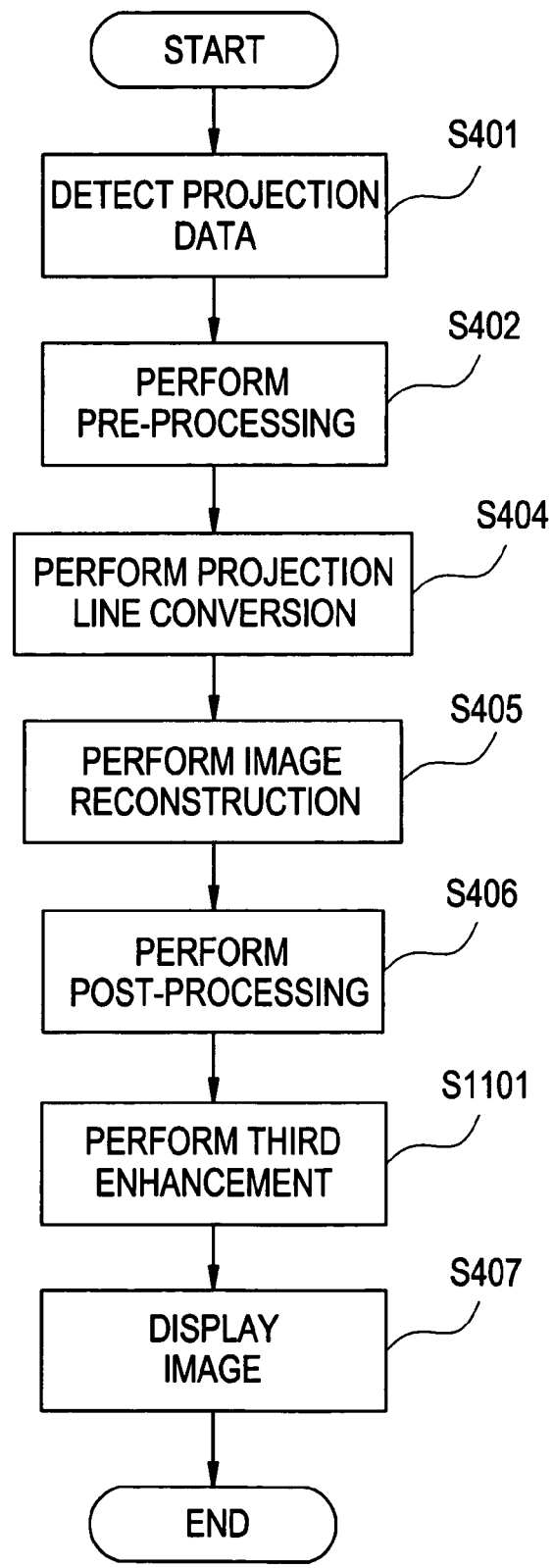
FIG. 11 is a flowchart describing actions to be performed by the data processing device according to the third embodiment.

FIG. 11 is a flowchart describing actions to be performed by the data processing device 60 included in the third embodiment. The flowchart of FIG. 11 is different from the flowchart of FIG. 4 concerning the first embodiment in a point that the first enhancement of step S403 is excluded and a point that the third enhancement is newly added to succeed step S406 of post-processing. Since steps S401 to S406 in FIG. 11 are identical to those described in FIG. 4 except step S403, the iterative description of the identical steps will be omitted. Steps succeeding step S406 at which tomographic image data is completed through post-processing will be described below.

Figure 12:
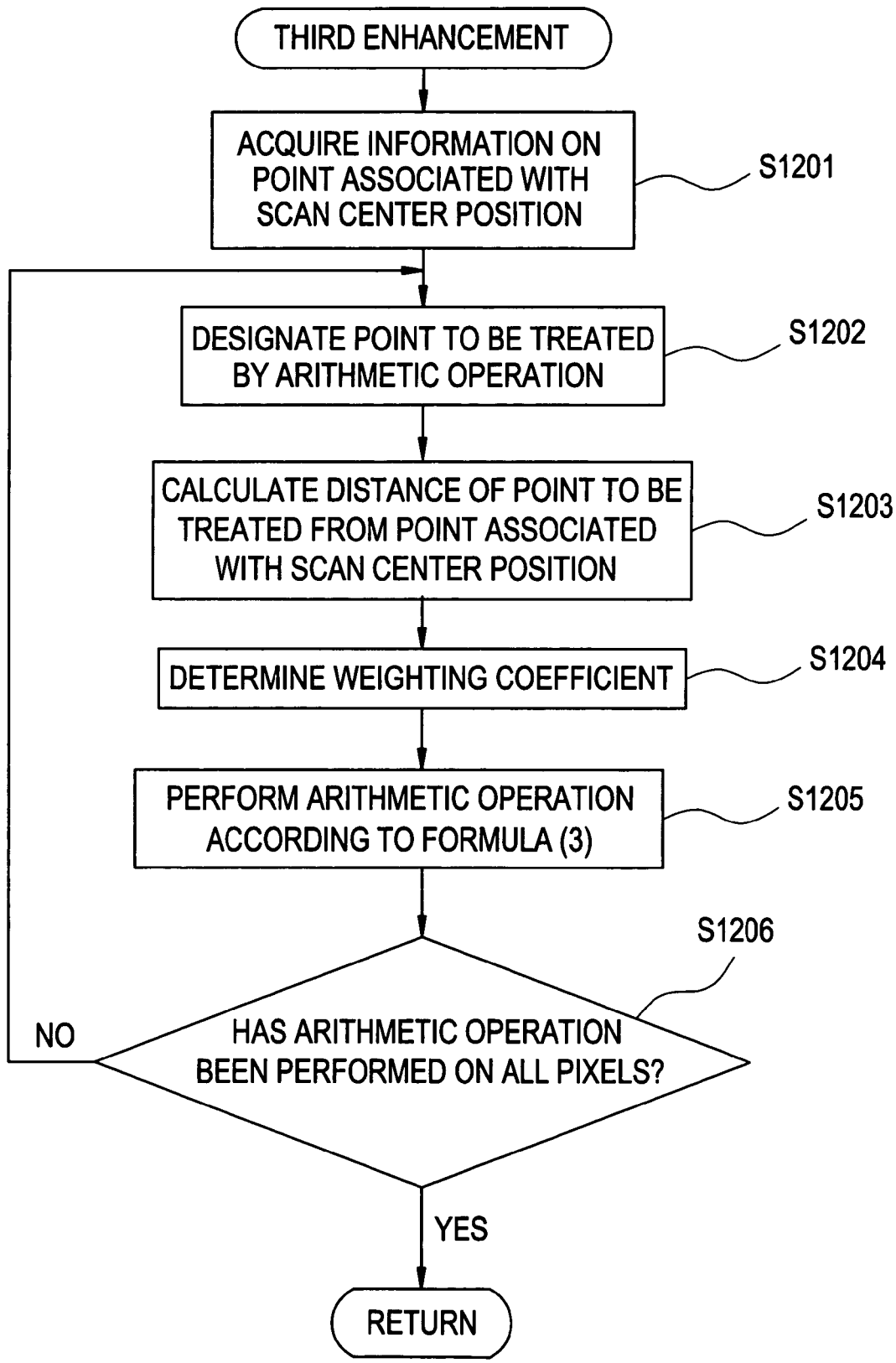
FIG. 12 is a flowchart describing actions to be performed during the third enhancement according to the third embodiment.

The data processing device 60 performs the third enhancement on tomographic image data produced at step S406 (step S1101). FIG. 12 is a flowchart describing actions to be performed during the third enhancement. First, the data processing device 60 acquires information on a point in an image represented by tomographic image data which is associated with a scan center position (step S1201). The scan center position is a center of rotation made by the rotator 34. The information on the point associated with the scan center position is acquired from the center of a tomographic image during image reconstruction of step S405.

Thereafter, the data processing device 60 designates a point in tomographic image data to be treated by an arithmetic operation (step S1202). The point to be treated lies in a two-dimensional image domain contained in tomographic image data. Every time the point to be treated is re-designated, the point to be treated is sequentially shifted to another untreated point within the image domain.

Thereafter, the data processing device 60 calculates a distance d of the point to be treated from the point associated with the scan center position (step S1203). The data processing device 60 retrieves a weighting coefficient $W_k(d)$ associated with the distance (step S1204), and performs an arithmetic operation (step S1205). The arithmetic operation is expressed with the following formula:

$$E_{l,m} = \sum_{k} I_{l,m} \times W_k(d) \quad \text{[Formula 1]}$$

where (l,m) denotes coordinates representing the location of a pixel in two-dimensional tomographic image data, $I_{l,m}$ denotes the value of the pixel, k denotes a parameter indicating a range of pixel values in a two-dimensional domain which is centered on the pixel concerned and which is treated by the arithmetic operation, and $W_k(d)$ denotes a weighting coefficient that varies depending on the distance d from the point associated with the scan center position. Moreover, $E_{l,m}$ denotes the treated value of a pixel whose location is represented by the coordinates (l,m).

Herein, the weighting coefficient $W_k(d)$ serves as a high-pass spatial filter that is a so-called convolution kernel. The high-pass property of the weighting coefficient $W_k(d)$ is such that the longer the distance d gets, the greater a degree of sharpening is. In order to increase the degree of sharpening, the weighting coefficient $W_k(d)$ is increased or the parameter k indicating a range of pixel values in a two-dimensional domain which is treated by an arithmetic operation is expanded.

Thereafter, the data processing device 60 checks all pixels to see if they have been treated by an arithmetic operation (step S1206). If the arithmetic operation has not been performed on all pixels (in the negative at step S1206), after the point to be treated is updated at step S1202, the arithmetic operation is performed again. If the arithmetic operation has been performed on all pixels (in the affirmative at step S1206), the arithmetic operation is terminated. Control is returned to the processing described in the flowchart of FIG. 11. A tomographic image is displayed based on enhanced tomographic image data, and the processing is terminated.

As mentioned above, according to the third embodiment, projection line conversion is performed in order to convert fan-beam data into parallel-beam data. The projection line conversion is succeeded by image reconstruction. The resultant tomographic image data is enhanced according to a distance of a point in an image from a point associated with a scan center position. Consequently, striped artifacts derived from the projection line conversion and occurring during implementation of the MIP method can be minimized. Moreover, a decrease in a resolution occurring at a point far away from the point associated with the scan center position can be reduced.

FOURTH EMBODIMENT

According to the first and second embodiments, the first or second enhancement is performed on projection data items contained in fan-beam data and identified with view numbers or row numbers in order to reduce a decrease in a resolution occurring in a reconstructed tomographic image. Local transmissible region data representing a local region of a subject may be sampled from fan-beam data, and local tomographic image data may be produced through image reconstruction of the local transmissible region data. In this case, the local transmissible region data may be Fourier-transformed in order to produce local frequency-domain data, and the local frequency-domain data may be enhanced or sharpened. According to the fourth embodiment, the fourth enhancement is performed on the local frequency-domain data for the purpose of sharpening.

A hardware configuration and acquired data items employed in the fourth embodiment of the present invention are identical to those shown in FIG. 1 to FIG. 3. An iterative description will be omitted. Moreover, a flowchart describing actions to be performed by the data processing device 60 is identical to the flowchart of FIG. 4 except that the fourth enhancement is substituted for the first enhancement of step S403. The description of the identical steps will be omitted. Only actions to be performed during the fourth enhancement at step S403 will be described below.

FIG. 13 is a flowchart describing actions to be performed during the fourth enhancement employed in the fourth embodiment. First, the fourth enhancement means included in the data processing device 60 samples local transmissible region data from fan-beam data (step S1301). The local transmissible region data is calculated from region data representing a local tomographic image which an operator delineates using the operating device 70. Projection data that is contained in fan-beam data shown in FIG. 3 and that represents the same region as the region data is sampled from the fan-beam data.

Thereafter, the data processing device 60 performs Fourier transform on the local transmissible region data (step S1302). This results in local frequency-domain data that is data produced by defining the local transmissible region data in a frequency domain. The data processing device 60 performs high-pass filtering on the local frequency-domain data (step S1303). Consequently, a low-frequency component contained in the local transmissible region data is readily removed owing to the employment of the local frequency-domain data.

Thereafter, the data processing device 60 performs inverse Fourier transform on the local frequency-domain data having undergone high-pass filtering (step S1304) so as to produce sharpened local transmissible region data having the low-frequency component thereof removed.

Thereafter, control is passed to step S404 described in FIG. 4. Projection line conversion and image reconstruction are performed on the sharpened local transmissible region data in order to produce local tomographic image data. A tomographic image is then enlarged and displayed based on the produced image data.

As mentioned above, according to the fourth embodiment, the first enhancement of step S403 described in FIG. 4 is not performed. Instead, local transmissible region data based on which local tomographic image data is produced is Fourier-transformed in order to produce frequency-domain data, and the high-pass filtering is performed on the frequency-domain data. Thus, the local transmissible region data is sharpened. Consequently, image data representing a desired region which an operator delineates can be efficiently enhanced.

Moreover, according to the fourth embodiment, local transmissible region data is sampled from fan-beam data. Alternatively, local transmissible region data may be sampled from parallel-beam data in the same manner as the aforesaid one. The local transmissible region data may be used to produce local frequency-domain data and sharpened local transmissible region data.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray computed tomography (CT) image reconstruction method comprising:
    rotating a fan-shaped X-ray beam about a subject, the fan-shaped X-ray beam having a thickness with respect to an axis of the subject and irradiating the subject;
    acquiring fan-shaped beam data based on at least one X-ray beam irradiated from each of a plurality of successive angles of rotation and attenuated by the subject;
    enhancement processing of respective projection data acquired along each of a plurality of projection lines of the fan-shaped X-ray beam to sharpen the projection data to create enhanced fan-shaped beam data;
    producing parallel-beam data based on the enhanced fan-shaped beam data; and
    reconstructing an image using the parallel-beam data such that a resolution of the image is maintained as a distance between respective points within the image and a scan center position increases.

2. The X-ray CT image reconstruction method according to claim 1, wherein enhancement processing comprises a first enhancement processing for sharpening projection data between successive angles of rotation of the fan-shaped X-ray beam.

3. The X-ray CT image reconstruction method according to claim 2, wherein assuming that j denotes a view number indicating an angle of rotation, i denotes a channel number indicating a location at which each projection line is terminated, r denotes a row number indicating a location in a thick direction, $P_{i,j,r}$ denotes a fan-shaped beam data value identified with the view number j, channel number i, and row number r, w denotes a number width that is a range of view numbers j of views containing projection data items to be treated, k denotes a parameter with which a view number of a view containing projection data to be treated is designated, $W_k$ denotes a weighting coefficient associated with each view number, and $Q_{i,j,r}$ denotes a fan-shaped beam data value that is identified with the view number j, channel number i, and row number r and that has undergone the first enhancement processing, the first enhancement processing employs the following formula:

$$Q_{i,j,r} = \sum_{k=-W}^{k=W} P_{i,j+k,r} \times W_k.$$

4. The X-ray CT image reconstruction method according to claim 2, wherein enhancement processing comprises a second enhancement processing for sharpening projection data between adjacent -shaped beam data in a thickness direction.

5. The X-ray CT image reconstruction method according to claim 4, wherein assuming that j denotes a view number indicating an angle of rotation, i denotes a channel number indicating a location at which each projection line is terminated, r denotes a row number indicating a location in the thickness direction, $P_{i,j,r}$ denotes a fan-shaped beam data value identified with the view number j, channel number i, and row number r, w denotes a number width that is a range of row numbers r indicating locations in the thickness direction at which projection data items to be treated are detected, k denotes a parameter with which a row number indicating a location in the thickness direction at which projection data to be treated is detected is designated, $W_k$ denotes a weighting coefficient associated with each row number, and $R_{i,j,r}$ denotes a fan-shaped beam data value that is identified with the view number j, channel number i, and row number r and that has undergone the second enhancement processing, the second enhancement processing employs the following formula:

$$R_{i,j,r} = \sum_{k=-W}^{k=W} P_{i,j,r+k} \times W_k.$$

6. An X-ray computed tomography (CT) image reconstruction method comprising:
    rotating a fan-shaped X-ray beam about a subject, the fan-shaped X-ray beam having a thickness with respect to an axis of the subject and irradiating the subject;
    acquiring fan-shaped beam data based on X-ray beams that are irradiated from each of a plurality of successive angles of rotation and attenuated by the subject;
    producing parallel-beam data based on the fan-shaped beam data that includes projection data taken at each angle of rotation of the fan-shaped X-ray beam;
    enhancement processing the parallel-beam data associated with respective projection data acquired along each of a plurality of projection lines of the fan-shaped X-ray beam to sharpen the parallel-beam data to create enhanced fan-shaped beam data; and
    reconstructing an image using the enhanced parallel-beam data such that a resolution of the image is maintained as a distance between respective points within the image and a scan center position increases.

7. The X-ray CT image reconstruction method according to claim 6, wherein enhancement processing comprises an enhancement processing for sharpening between successive angles of rotation of the fan-shaped X-ray beam data.

8. The X-ray CT image reconstruction method according to claim 6, wherein enhancement processing comprises an enhancement processing for sharpening projection data between adjacent fan-shaped beam data in a thickness direction.

9. An X-ray computed tomography (CT) image reconstruction method comprising:

rotating a fan-shaped X-ray beam about a subject, the fan-shaped X-ray beam having a thickness with respect to an axis of the subject and irradiating the subject;

acquiring fan-shaped beam data based on X-ray beams that are irradiated from each of a plurality of successive angles of rotation and attenuated by the subject;

producing parallel-beam data based on the fan-shaped beam data that includes projection data taken at each angle of rotation of the fan-shaped X-ray beam;

reconstructing a tomographic image of the subject using the parallel-beam data;

identifying a scan center position equivalent to a center position of the tomographic image; and performing enhancement processing on pixels contained in the tomographic image associated with respective projection data acquired along each of a plurality projection lines of the fan-shaped X-ray beam to sharpen the tomographic image to enhance the fan-shaped beam data, wherein a degree of image sharpening increases as a distance from the scan center position increases.

10. An X-ray computed tomography (CT) system comprising:

a rotator configured to rotate a fan-shaped X-ray beam about a subject, the fan-shaped X-ray beam having a thickness with respect to an axis of the subject and irradiating the subject;

an X-ray detector configured to detect fan-shaped beam data based on X-ray beams that are irradiated from each of a plurality of successive angles of rotation and attenuated by the subject;

an enhancement device configured to process respective projection data acquired along each of a plurality of projection lines of the fan-shaped X-ray beam to sharpen the projection data to create enhanced fan-shaped beam data;

a projection line conversion device configured to produce parallel-beam data based on the enhanced fan-shaped beam data; and an image reconstruction device configured to reconstruct an image using the parallel-beam data such that a resolution of the image is maintained as a distance between respective points within the image and a scan center position increases.

11. The X-ray CT system according to claim 10, wherein said enhancement device is configured to perform an enhancement processing for sharpening projection data between successive angles of rotation of the fan-shaped X-ray beam.

12. The X-ray CT system according to claim 10, wherein said enhancement device is configured to perform an enhancement processing for sharpening projection data between adjacent fan-shaped beam data in a thickness direction.

13. An X-ray computed tomography (CT) system comprising:

a rotator configured to rotate a fan-shaped X-ray beam about a subject, the fan-shaped X-ray beam having a thickness with respect to an axis of the subject and irradiating the subject;

an X-ray detector configured to detect fan-shaped beam data based on X-ray beams that are irradiated from each of a plurality of successive angles of rotation and attenuated by the subject;

a projection line conversion device configured to produce parallel-beam data based on the enhanced fan-shaped beam data;

an enhancement device configured to enhance the parallel-beam data associated with respective projection data acquired along each of a plurality of projection lines of the fan-shaped X-ray beam to sharpen the parallel-beam data to create enhanced fan-shaped beam data; and an image reconstruction device configured to reconstruct an image using the enhanced parallel-beam data such that a resolution of the image is maintained as a distance between respective points within the image and a scan center position increases.

14. The X-ray CT system according to claim 13, wherein said enhancement device comprises a first enhancement device configured to perform a first enhancement processing for sharpening projection data between successive angles of rotation of the fan-shaped X-ray beam.

15. The X-ray CT system according to claim 14, wherein said enhancement device further comprises a second enhancement device configured to perform a second enhancement processing for sharpening projection data between adjacent fan-shaped beam data in a thickness direction.

16. An X-ray computed tomography (CT) system comprising:

a rotator configured to rotate a fan-shaped X-ray beam about a subject, the fan-shaped X-ray beam having a thickness with respect to a body axis of the subject and irradiating the subject;

an X-ray detector configured to detect fan-shaped beam data based on X-ray beams that are irradiated from each of a plurality of successive angles of rotation and attenuated by the subject;

a projection line conversion device configured to produce parallel-beam data based on the fan-shaped beam data;

an image reconstruction device configured to reconstruct a tomographic image of the subject using the parallel-beam data; and an enhancement device configured to identify a scan center position that is equivalent to a center position of the tomographic image and to perform enhancement processing on pixels contained in the tomographic image associated with respective projection data acquired along each of a plurality of projection lines of the fan-shaped X-ray beam to sharpen the tomographic image to enhance the tomographic image, wherein a degree of image sharpening increases as a distance from the scan center position increases.

* * * * *